US012679828B2

(12) United States Patent
Shin et al.

(10) Patent No.: US 12,679,828 B2
(45) Date of Patent: Jul. 14, 2026

(54) METHOD FOR PREPARING LIFITEGRAST

(71) Applicant: YONSUNG FINE CHEMICAL CO., LTD., Hwaseong-si (KR)

(72) Inventors: Hyun Ik Shin, Suwon-si (KR); Eun Im Jeong, Suwon-si (KR); Chang Heon Suhl, Suwon-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 1083 days.

(21) Appl. No.: 17/780,380

(22) PCT Filed: Nov. 20, 2020

(86) PCT No.: PCT/KR2020/016487

§ 371 (c)(1),
(2) Date: May 26, 2022

(87) PCT Pub. No.: WO2021/107514

PCT Pub. Date: Jun. 3, 2021

(65) Prior Publication Data

US 2023/0027871 A1 Jan. 26, 2023

(30) Foreign Application Priority Data

Nov. 27, 2019 (KR) ........................ 10-2019-0154793

(51) Int. Cl.
*C07D 405/06* (2006.01)

(52) U.S. Cl.
CPC .................................. *C07D 405/06* (2013.01)

(58) Field of Classification Search
CPC .................................................... C07D 405/06
See application file for complete search history.

(56) References Cited

U.S. PATENT DOCUMENTS 7,314,938 B2 1/2008 Shen et al.

FOREIGN PATENT DOCUMENTS

| | | | | |
|---|---|---|---|---|
| CN | 106995439 | A | | 8/2017 |
| WO | 2019/004936 | | * | 1/2019 |
| WO | 2019/004936 | A1 | | 1/2019 |
| WO | 2019/043724 | A1 | | 3/2019 |
| WO | 2019/097547 | | * | 5/2019 |
| WO | 2019/097547 | A1 | | 5/2019 |
| WO | 2019/186520 | A1 | | 10/2019 |

OTHER PUBLICATIONS

International Search Report for PCT/KR2020/016487 dated, May 7, 2021 (PCT/ISA/210).

* cited by examiner

*Primary Examiner* — D Margaret M Seaman
(74) *Attorney, Agent, or Firm* — Sughrue Mion, PLLC

(57) ABSTRACT

An improved method for preparing lifitegrast is provided. The method is efficient and cost-effective and produces lifitegrast with high purity.

14 Claims, No Drawings

METHOD FOR PREPARING LIFITEGRAST

CROSS REFERENCE TO RELATED APPLICATIONS

This application is a National Stage of International Application No. PCT/KR2020/016487 filed Nov. 20, 2020, claiming priority based on Korean Patent Application No. 10-2019-0154793 filed Nov. 27, 2019.

TECHNICAL FIELD

The present invention relates to a process for preparing lifitegrast. More particularly, the present invention relates to an efficient and cost-effective process for preparing lifitegrast with high purity.

BACKGROUND ART

Lifitegrast of the following formula (1) ((S)-2-(2-(benzofuran-6-carbonyl)-5,7-dichloro-1,2,3,4-tetrahydroisoquinoline-6-carboxamido)-3-(3-(methylsulfonyl)phenyl)propanoic acid) is an active pharmaceutical ingredient of Xiidra®, which is a medicine for keratoconjunctivitis sicca.

(1)

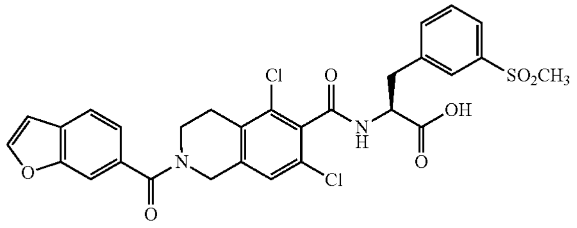

U.S. Pat. No. 7,314,938, which relates to a derivative of lifitegrast and a preparation process therefor, discloses a process for preparing lifitegrast. The patent describes a process for preparing lifitegrast using an amide coupling reagent such as EDC and HATU.

However, the preparation process has problems that the amide coupling reagent such as HATU is very expensive, the yield is low due to low reactivity, and the purity of generated lifitegrast is low, so that it is difficult to be applied for mass production.

DISCLOSURE

Technical Problem

The inventors have endeavored to solve the above problems in the preparation of lifitegrast, and found that lifitegrast can be prepared with high purity and high yield without using expensive reagents by chlorination in the presence of a tertiary amine and in situ amide coupling.

Accordingly, it is an object of the present invention to provide an efficient and cost-effective process for preparing lifitegrast with high purity.

Technical Solution

One embodiment of the present invention relates to a process for preparing a compound of the following formula (1), which comprises the steps of:

(i) chlorinating a carboxyl group of a compound of the following formula (2) and subjecting a compound of the following formula (3) to amide coupling therewith to obtain a compound of the following formula (4);

(ii) subjecting the compound of the following formula (4) to demethylation to obtain a compound of the following formula (5);

(iii) chlorinating a carboxyl group of the compound of the following formula (5) in the presence of a tertiary amine and subjecting a compound of the following formula (6) to amide coupling therewith to obtain a compound of the following formula (7); and (iv) subjecting an ester group of the compound of the following formula (7) to hydrolysis:

(2)

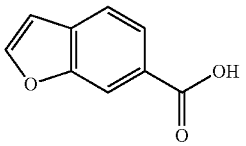

(3)

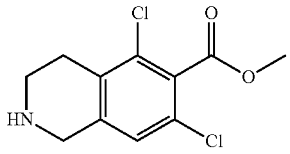

(4)

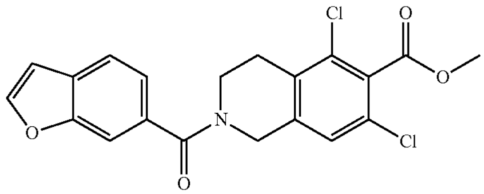

(5)

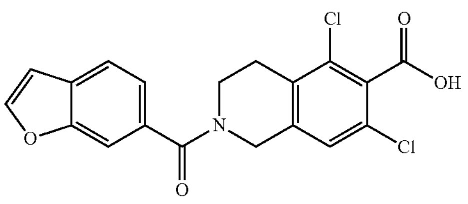

-continued
(6)
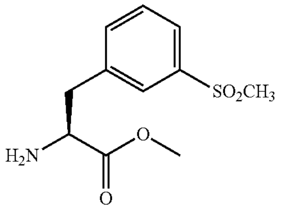
(7)
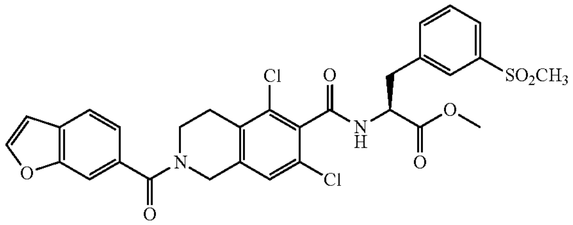
-continued
(1)
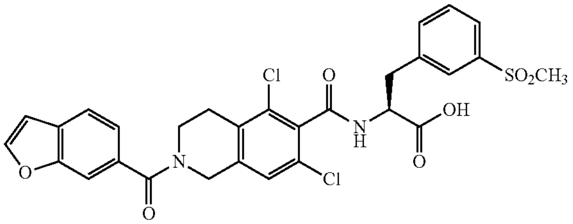
Hereinafter, the preparation process of the present invention is described in more detail referring to the following reaction scheme 1. The process depicted in the following reaction scheme 1 represents merely a typical example, and various changes may be made to reagents and reaction conditions without limitation.
[Reaction Scheme 1]
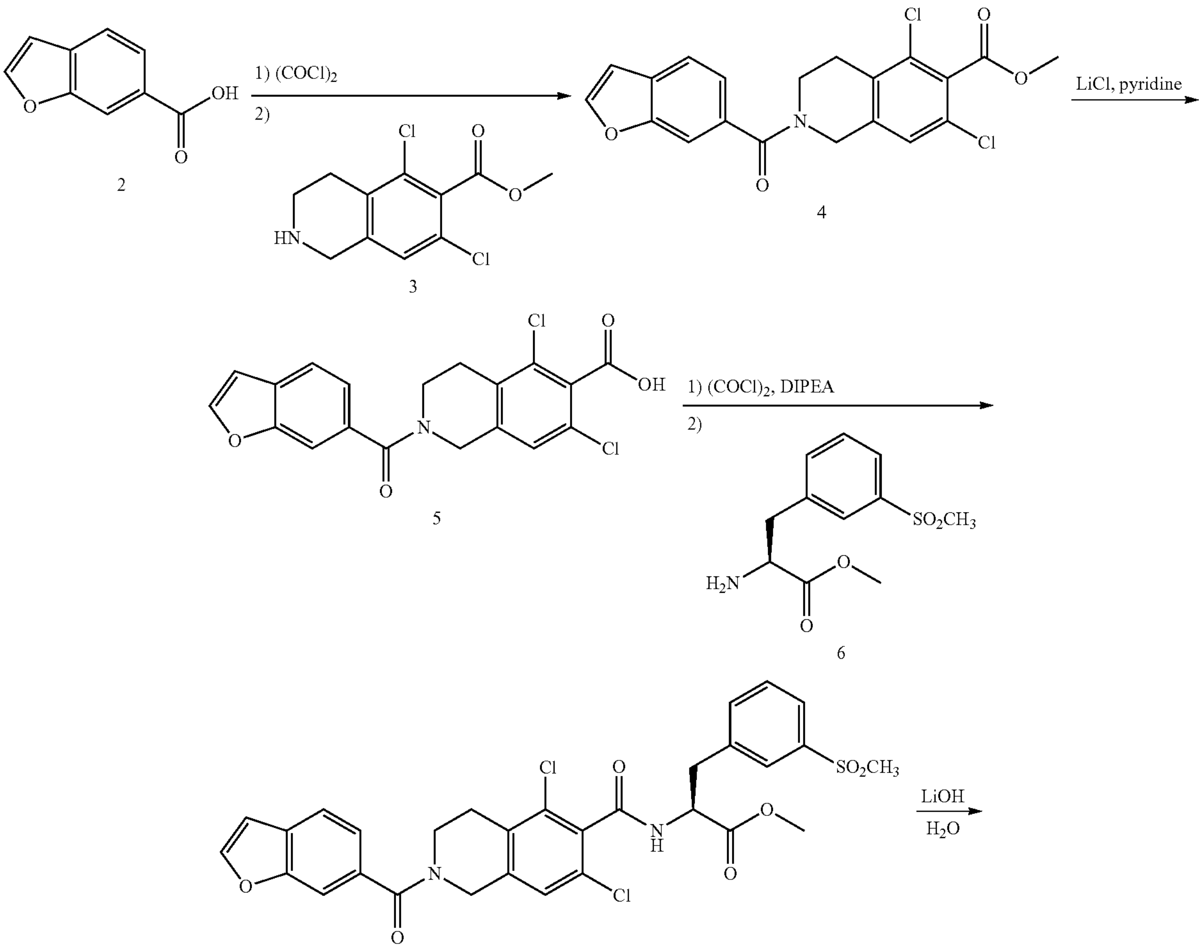
2 3 4 5 6 7

-continued

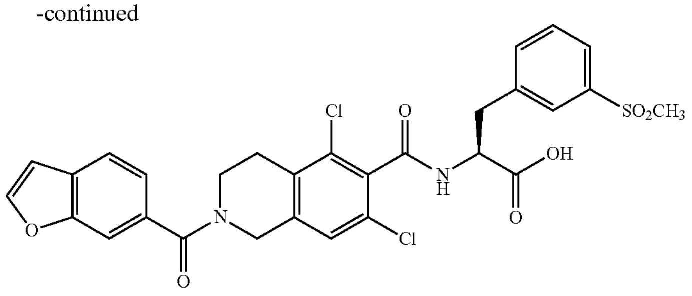

1

Step 1: Synthesis of Compound of Formula (4)

The compound of formula (4) can be prepared by chlorinating the carboxyl group of the compound of formula (2) and subjecting the compound of formula (3) to amide coupling therewith.

The chlorination can be carried out using oxalyl chloride, thionyl chloride, phosphorus trichloride, phosphorus pentachloride, etc. Particularly, oxalyl chloride is preferred.

Further, the chlorination can be carried out in the presence of dimethylformamide as a catalyst.

The compound prepared by the chlorination is used for the following amide coupling in the same reactor (in situ) without further separation process.

The amide coupling can be carried out in the presence of a base.

As the base, triethylamine, diisopropylethylamine, 4-methylmorpholine, etc. may be used. Particularly, diisopropylethylamine is preferred.

The compound of formula (3) can be in a form of a salt. For instance, the compound of formula (3) can be in a form of hydrochloride.

As the reaction solvent for the chlorination and amide coupling, dichloromethane, chloroform, toluene, etc. may be used. Particularly, toluene is preferred.

The chlorination is preferably carried out at room temperature, and the amide coupling is preferably carried out at 0 to 5° C.

The prepared compound of formula (4) may be purified by recrystallization using toluene. The recrystallization can be carried out by heating toluene in which the compound of formula (4) is dissolved to 80° C., followed by cooling to 0 to 10° C.

Meanwhile, the compound of formula (2) and the compound of formula (3) as starting materials may be synthesized by means known in the art [see U.S. Pat. No. 7,314,938] or commercially available.

Step 2: Synthesis of Compound of Formula (5)

The compound of formula (5) can be prepared by subjecting the compound of formula (4) to demethylation.

The demethylation may be carried out using lithium halide such as lithium chloride and lithium iodide.

As the reaction solvent, dimethylformamide, tetraethylene glycol, triethylene glycol, etc. may be used. Particularly, dimethylformamide is preferred.

Further, the demethylation may be carried out in the presence of a base.

As the base, pyridine may be used, but it is not limited thereto.

The reaction temperature is suitably 80 to 100° C., and the reaction time is preferably about 36 to 48 hours.

The prepared compound of formula (5) can be purified by acidification and solidification using 37% HCl aqueous solution.

Step 3: Synthesis of Compound of Formula (7)

The compound of formula (7) can be prepared by chlorinating the carboxyl group of the compound of formula (5) in the presence of a tertiary amine and subjecting the compound of the following formula (6) to amide coupling therewith.

The chlorination may be carried out using oxalyl chloride, thionyl chloride, phosphorus trichloride, phosphorus pentachloride, etc. Particularly, oxalyl chloride is preferred.

As the tertiary amine, diisopropylethylamine, triethylamine, dimethylaniline, 4-methylmorpholine, etc. may be used. Particularly, diisopropylethylamine is preferred.

The compound prepared by the chlorination is used for the following amide coupling in the same reactor (in situ) without further separation process.

In accordance with an embodiment of the present invention, the solubility and reactivity of the compound of formula (5) can be increased by using the tertiary amine for chlorination, thereby improving yield and purity.

The amide coupling may be carried out in the presence of a base.

As the base, triethylamine, diisopropylethylamine, 4-methylmorpholine, etc. may be used. Particularly, diisopropylethylamine is preferred.

The compound of formula (6) can be in a form of a salt. For instance, the compound of formula (6) can be in a form of hydrochloride.

As the reaction solvent for the chlorination and amide coupling, dichloromethane, chloroform, toluene, tetrahydrofuran, etc. may be used. Particularly, dichloromethane is preferred.

The chlorination is preferably carried out at 0 to 5° C., and the amide coupling is preferably carried out at room temperature.

The prepared compound of formula (7) may be purified by recrystallization using butanone. The recrystallization can be carried out by adding butanone to the compound of formula (7) and heating it to 40° C., followed by cooling to 15 to 30° C.

Meanwhile, the compound of formula (6) may be synthesized by means known in the art [see U.S. Pat. No. 7,314,938] or commercially available.

Step 4: Synthesis of Compound of Formula (1)

The compound of formula (1) can be prepared by subjecting the ester group of the compound of formula (7) to hydrolysis.

The hydrolysis may be carried out in the presence of a base.

As the base, lithium hydroxide, potassium hydroxide, sodium hydroxide, etc. may be used. Particularly, lithium hydroxide is preferred.

As the reaction solvent, methanol, ethanol, propanol, tetrahydrofuran, water, etc. may be used. Particularly, a mixed solvent of tetrahydrofuran and water is preferred.

The reaction temperature is suitably 0 to 5° C.

The prepared compound of formula (1) can be purified by acidification and solidification using 37% HCl aqueous solution.

The purity of the prepared compound of formula (1) may be 99.0% or more, preferably 99.6% or more. Further, the optical purity may be 99% or more.

One embodiment of the present invention relates to a process for preparing a compound of the following formula (1), which comprises the steps of.

(iii) chlorinating a carboxyl group of a compound of the following formula (5) in the presence of a tertiary amine and subjecting a compound of the following formula (6) to amide coupling therewith to obtain a compound of the following formula (7); and (iv) subjecting an ester group of the compound of the following formula (7) to hydrolysis:

(5)

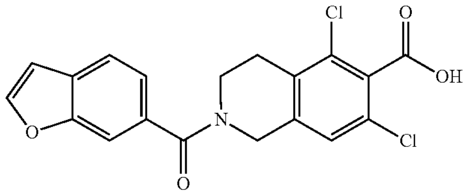

(6)

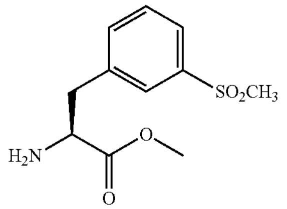

(7)

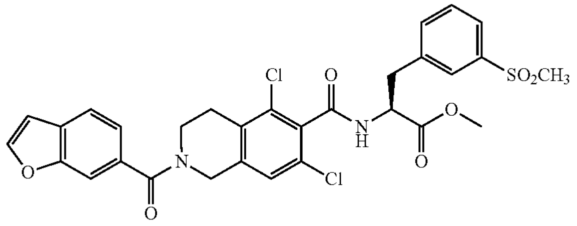

(1)

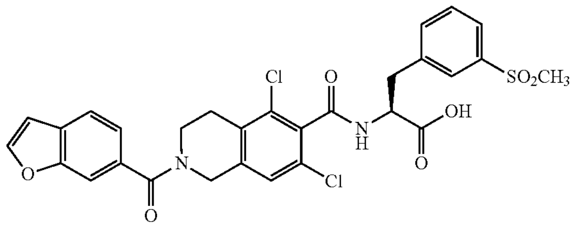

The process includes the same steps (iii) and (iv) as in the above process for preparing the compound of formula (1), and thus a detailed description thereof will be omitted to avoid repetition.

Advantageous Effects

In accordance with the preparation process of the present invention, lifitegrast having 99.0% or more of purity can be prepared efficiently and cost-effectively by chlorination in the presence of a tertiary amine and in situ amide coupling without using expensive reagents.

BEST MODE

The present invention will be described in more detail by following examples. It will be obvious to those skilled in the art that these examples are merely described for illustration of the present invention and the scope of the present invention is not limited thereto.

Example 1: Preparation of Compound of Formula (4

Benzofuran-6-carboxylic acid (2) (81.36 g, 501.8 mmol) was suspended in toluene (407 mL, 5 v/w) and dimethylformamide (1.95 mL, 25.09 mmol), and oxalyl chloride (51.64 mL, 602.2 mmol) was slowly added dropwise thereto, followed by stirring at room temperature for 2 hours. When the reaction was terminated, methyl 5,7-dichloro-1,2,3,4-tetrahydroisoquinoline-6-carboxylate hydrochloride (3) (148.8 g, 501.8 mmol) and toluene (407 mL, 5 v/w) were added to the resulting solution, and the temperature in the reactor was cooled to 0° C. Diisopropylethylamine (288.5 mL, 1656 mmol) was slowly added dropwise thereto, followed by stirring for 1 hour. After confirming the termination of the reaction by HPLC, the resulting solution was warmed to room temperature, and 20% NaOH solution was added thereto. The resulting solution was heated to 80° C., followed by stirring until the suspension became transparent. After stopping the reaction, the aqueous layer was separated, and water (81 mL, 1 v/w) was added to the organic layer to wash once again. While the washed organic layer was stirred, the temperature of the resulting solution was raised to 80° C. to dissolve completely, followed by stopping stirring and cooling slowly to room temperature. When the temperature was cooled to 50° C. or less and a solid was generated, it was stirred at 60 rpm for 12 hours or more. After stirring for 12 hours or more, the resulting solution was cooled slowly from room temperature to 0° C. When the area % of methyl 2-(benzofuran-6-carbonyl)-5,7-dichloro-1,2,3,4-tetrahydroisoquinoline-6-carboxylate (4) in the supernatant was not changed by HPLC, the stirring was stopped, followed by filtration. The filtered solid was washed 6 times with toluene (486 mL, 6 v/w). The obtained solid was dried in a vacuum for 12 hours or more to give the compound of formula (4) (168.8 g, 417.6 mmol, 83.3%), which is a white crystalline solid.

1H NMR (300 MHz, DMSO): δ 8.13 (1H, d, J=2.4 Hz), 7.77 (1H, s), 7.75 (1H, d, J=3.0 Hz), 7.55 (1H, bs), 7.37 (1H, d, J=8.1 Hz), 7.05 (1H, q, J=6.0 Hz, J=2.1 Hz), 4.80 (2H, bs), 3.93 (3H, s), 3.74 (2H, bs), 2.86 (2H, t, J=5.7 Hz); 13C NMR (300 MHz, DMSO): δ=169.92, 165.17, 154.12, 148.17, 138.98, 132.98, 132.07, 131.71, 130.97, 129.13, 128.00, 126.66, 122.51, 121.86, 110.83, 107.29, 53.64.

Example 2: Preparation of Compound of Formula (5

Methyl 2-(benzofuran-6-carbonyl)-5,7-dichloro-1,2,3,4-tetrahydroisoquinoline-6-carboxylate (4) (3 g, 7.42 mmol) and lithium chloride (2.359 g, 55.65 mmol) were suspended in dimethylformamide (15 mL, 5 v/w), and pyridine (1.8 mL, 22.26 mmol) was added dropwise thereto, followed by heating to 90° C. and stirring for 48 hours. After confirming the termination of the reaction by HPLC, the resulting solution was cooled to room temperature, and methyl tert-butyl ether (6 mL, 2 v/w) and water (6 mL, 2 v/w) were added dropwise thereto, followed by washing while stirring for 30 minutes. The aqueous layer was separated and washed once again with methyl tert-butyl ether (6 mL, 2 v/w), followed by separating and removing the organic layer. Concentration was carried out to remove the organic layer remaining in the aqueous layer. Acidification and solidification were carried out by slowly adding dropwise 37% HCl aqueous solution (9 mL, 3 v/w) to the aqueous layer, while stirring rapidly. When pH was decreased to 1 or less, stirring was stopped, followed by filtration. The filtered solid was washed with water (21 mL, 7 v/w). The obtained solid was dried in a vacuum at 60° C. for 12 hours or more to give 2-(benzofuran-6-carbonyl)-5,7-dichloro-1,2,3,4-tetrahydroisoquinoline-6-carboxylic acid (5) (2.7 g, 6.919 mmol, 93%), which is a light brown solid.

1H NMR (300 MHz, DMSO): δ 8.12 (1H, d, J=2.1 Hz), 7.76 (1H, s), 7.74 (1H, s), 7.49 (1H, bs), 7.35 (1H, d, J=8.1 Hz), 7.05 (1H, q, J=6.0 Hz, J=2.3 Hz), 4.76 (2H, bs), 3.71 (2H, bs), 2.85 (2H, t, J=5.7 Hz); 13C NMR (300 MHz, DMSO): δ=169.92, 165.17, 154.12, 148.17, 138.98, 132.98, 132.07, 131.71, 130.97, 129.13, 128.00, 126.66, 122.51, 121.86, 110.83, 107.29.

Example 3: Preparation of Compound of Formula (7

2-(benzofuran-6-carbonyl)-5,7-dichloro-1,2,3,4-tetrahydroisoquinoline-6-carboxylic acid (5) (5 g, 12.81 mmol) was dissolved in dichloromethane (50 mL, 10 v/w) and diisopropylethylamine (2.45 mL, 14.09 mmol), followed by cooling to 0° C.

Oxalyl chloride (1.21 mL, 14.09 mmol) was slowly added dropwise to the resulting solution while maintaining 5° C. or less, followed by stirring at 0° C. for 5 hours and 30 minutes. After the termination of the reaction, (S)-methyl 2-amino-3-(3-(methylsulfonyl)phenyl)propionate hydrochloride (6) (4.14 g, 14.09 mmol) was added to the resulting solution. Diisopropylethylamine (4.91 mL, 28.18 mmol) was slowly added dropwise to the resulting solution while maintaining 5° C. or less. The resulting solution was warmed to room temperature, followed by stirring for 2 hours and 30 minutes. After confirming the termination of the reaction by HPLC, water (50 mL, 10 v/w) was added dropwise to the resulting solution, followed by stirring for 30 minutes. The organic layer was separated and washed with iN HCl aqueous solution (25 mL, 5 v/w) and $NaHCO_3$ saturated aqueous solution (25 mL, 5 v/w), respectively. At this time, it was washed repeatedly with $NaHCO_3$ saturated aqueous solution (25 mL, 5 v/w) until the area % of 2-(benzofuran-6-carbonyl)-5,7-dichloro-1,2,3,4-tetrahydroisoquinoline-6-carboxylic acid (5) reached 0.28% or less by HPLC. The organic layer was separated and concentrated, and azeotropic distillation was carried out using butanone (15 mL, 3 v/w) to substitute with butanone (15 mL, 3 v/w) finally. After warming the resulting solution to 40° C. and stirring until it is dissolved, it was slowly cooled to room temperature while stirring at 80 rpm. After 12 hours, when the area % of (S)-methyl 2-(2-(benzofuran-6-carbonyl)-5,7-dichloro-1,2,3,4-tetrahydroisoquinoline-6-carboxamido)-3-(3-(methylsulfonyl)phenyl)propionate (7) in the supernatant reached about 20% or less by HPLC, the stirring was stopped, followed by filtration. The filtered solid was washed with methyl tert-butyl ether. The obtained solid was dried in a vacuum at 35° C. for 12 hours or more to give the compound of formula (7) (6.612 g, 10.50 mmol, 82%), which is a crystalline solid.

1H NMR (300 MHz, DMSO): δ 9.15 (1H, d, J=8.1 Hz), 8.12 (1H, d, J=2.4 Hz), 7.87 (1H, s). 7.80-7.66 (4H, m), 7.58 (1H, t, J=7.8 Hz), 7.34-7.32 (2H, m), 7.05 (1H, d, J=1.5 Hz), 4.90-4.74 (3H, bm), 3.69 (3H, s), 3.29-3.28 (1H, m), 3.16 (3H, s), 3.10-3.02 (1H, m), 2.78 (2H, m); 13C NMR (300 MHz, DMSO): δ=171.54, 164.12, 154.13, 148.21, 141.18, 139.24, 137.66, 134.90, 134.78, 132.22, 132.01, 131.60, 129.77, 129.15, 128.85, 128.20, 126.25, 125.61, 122.49, 121.91, 110.80, 107.31, 53.47, 52.46, 44.07, 36.50, 36.33, 29.80, 8.14.

Example 4: Preparation of Compound of Formula (1

(S)-methyl 2-(2-(benzofuran-6-carbonyl)-5,7-dichloro-1,2,3,4-tetrahydroisoquinoline-6-carboxamido)-3-(3-(methylsulfonyl)phenyl)propionate (7) (1 g, 1.589 mmol) was suspended in tetrahydrofuran (5 mL, 5 v/w), followed by cooling to 0° C. 1M LiOH aqueous solution (1.75 mL, 1.747 mmol) was slowly added dropwise to the resulting solution while maintaining 5° C. or less, followed by stirring at 0° C. for 2 hours. After confirming the termination of the reaction by HPLC, the resulting solution was warmed to room temperature. The resulting solution was concentrated, and water (5 mL, 5 v/w), $NaHCO_3$ saturated aqueous solution (1 mL, 1 v/w) and ethyl acetate (3 mL, 3 v/w) were added dropwise thereto, followed by washing while stirring for 30 minutes. The aqueous layer was separated and washed once again with ethyl acetate (3 mL, 3 v/w), followed by separating and removing the organic layer. Concentration was carried out to remove the organic layer remaining in the aqueous layer. Acidification and solidification were carried out by slowly adding dropwise 37% HCl aqueous solution (3 mL, 3 v/w) to the aqueous layer, while stirring rapidly. When pH was decreased to 1 or less, dichloromethane (10 mL, 10 v/w) was slowly added dropwise thereto, followed by stirring for 30 minutes. The organic layer was separated and concentrated, and azeotropic distillation was carried out 3 times using butanone (2 mL, 2 v/w). Butanone (6 mL, 6 v/w) was added thereto, and recrystallization was carried out at room temperature while stirring at 60 rpm. After stirring for 3 days, when the area % of (S)-2-(2-(benzofuran-6-carbonyl)-5,7-dichloro-1,2,3,4-tetrahydroisoquinoline-6-carboxamido)-3-(3-(methylsulfonyl)propionic acid (1) in the supernatant was not changed by HPLC, the stirring was stopped, followed by filtration. The filtered solid was washed with butanone (2 mL, 2 v/w) and water (2 mL, 2 v/w), respectively. The obtained solid was dried in a vacuum for 12 hours or more to give the compound of formula (1) (0.73 g, 1.192 mmol, 75%, purity: 99.6%, optical purity: 99.1%), which is a white crystalline solid.

1H NMR (300 MHz, DMSO): δ 12.87 (1H, bs), 9.01 (1H, d, J=8.1 Hz), 8.12 (1H, d, J=2.4 Hz), 7.87 (1H, s). 7.78-7.67 (4H, m), 7.57 (1H, t, J=7.8 Hz), 7.34 (2H, m), 7.04 (1H, d, J=1.5 Hz), 4.82-4.73 (3H, bm), 3.29-3.27 (1H, m), 3.15 (3H, s), 3.07-3.02 (1H, m), 2.77 (2H, m); 13C NMR (300 MHz, DMSO): δ=172.55, 169.94, 164.05, 154.11, 148.21, 141.10, 139.56, 137.51, 134.99, 134.94, 132.14, 132.05, 131.62, 129.74, 129.16, 128.86, 128.20, 126.18, 125.53, 122.48, 121.92, 110.80, 107.32, 53.52, 44.09, 36.82.

The invention claimed is:

1. A process for preparing a compound of the following formula (1), which comprises the steps of:

(i) chlorinating a carboxyl group of a compound of the following formula (2) and subjecting a compound of the following formula (3) to amide coupling therewith to obtain a compound of the following formula (4);

(ii) subjecting the compound of the following formula (4) to demethylation to obtain a compound of the following formula (5);

(iii) chlorinating a carboxyl group of the compound of the following formula (5) in the presence of a tertiary amine, subjecting a compound of the following formula (6) to amide coupling therewith to obtain a compound of the following formula (7), and recrystallizing the compound of the following formula (7) using butanone; and (iv) subjecting an ester group of the compound of the following formula (7) to hydrolysis to obtain the compound of the following formula (1), wherein the compound of formula (1) has a purity of 99.6% or more:

(2)

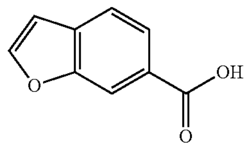

(3)

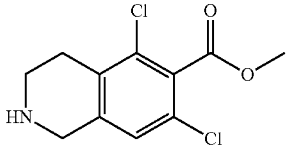

(4)

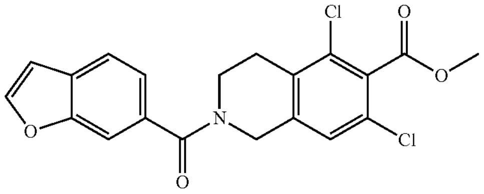

(5)

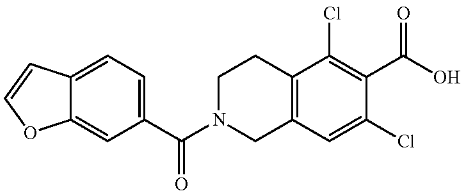

(6)

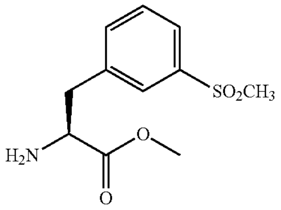

-continued (7)

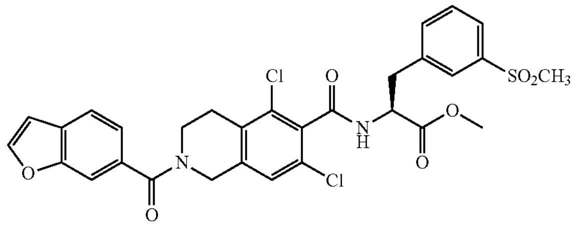

(1)

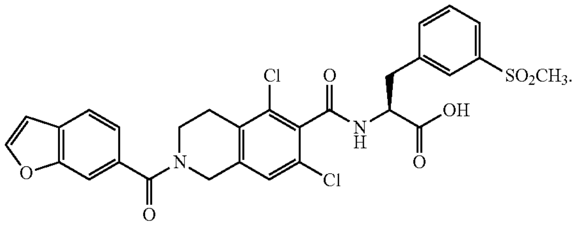

2. The process according to claim 1, wherein the chlorination of step (i) is carried out using oxalyl chloride.

3. The process according to claim 1, wherein the compound of formula (3) of step (i) is in a form of hydrochloride.

4. The process according to claim 1, wherein the amide coupling of step (i) is carried out in the presence of a base.

5. The process according to claim 4, wherein the base is diisopropylethylamine.

6. The process according to claim 1, wherein the demethylation of step (ii) is carried out using lithium halide.

7. The process according to claim 1, wherein the tertiary amine of step (iii) is diisopropylethylamine.

8. The process according to claim 1, wherein the chlorination of step (iii) is carried out using oxalyl chloride.

9. The process according to claim 1, wherein the compound of formula (6) of step (iii) is in a form of hydrochloride.

10. The process according to claim 1, wherein the amide coupling of step (iii) is carried out in the presence of a base.

11. The process according to claim 10, wherein the base is diisopropylethylamine.

12. The process according to claim 1, wherein the hydrolysis of step (iv) is carried out in the presence of a base.

13. The process according to claim 12, wherein the base is lithium hydroxide.

14. A process for preparing a compound of the following formula (1), which comprises the steps of:

(iii) chlorinating a carboxyl group of a compound of the following formula (5) in the presence of a tertiary amine, subjecting a compound of the following formula (6) to amide coupling therewith to obtain a compound of the following formula (7), and recrystallizing the compound of the following formula (7) using butanone; and (iv) subjecting an ester group of the compound of the following formula (7) to hydrolysis to obtain the compound of the formula (1), wherein the compound of formula (1) has a purity of 99.6% or more:

(5)
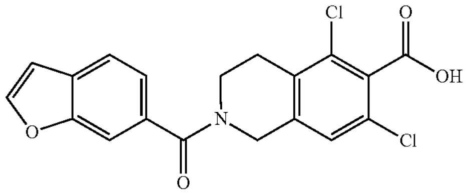
(6)
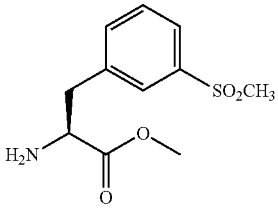
-continued
(7)
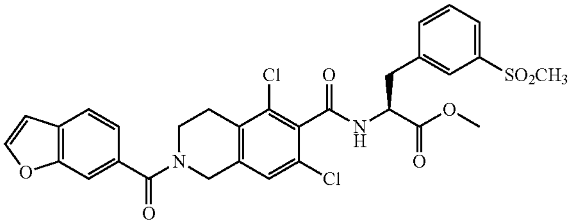
(1)
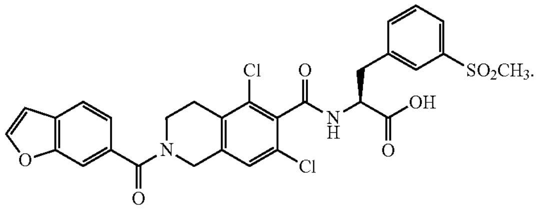
* * * * *